United States Patent
Martin

(10) Patent No.: US 8,296,083 B2
(45) Date of Patent: Oct. 23, 2012

(54) VIBRATORY PIPELINE DIAGNOSTIC SYSTEM AND METHOD

(75) Inventor: John D Martin, Longmont, CO (US)

(73) Assignee: Micro Motion, Inc., Boulder, CO (US)

( * ) Notice: Subject to any disclaimer, the term of this patent is extended or adjusted under 35 U.S.C. 154(b) by 406 days.

(21) Appl. No.: 12/526,103

(22) PCT Filed: Feb. 22, 2007

(86) PCT No.: PCT/US2007/062590
§ 371 (c)(1),
(2), (4) Date: Aug. 6, 2009

(87) PCT Pub. No.: WO2008/103176
PCT Pub. Date: Aug. 28, 2008

(65) Prior Publication Data
US 2010/0324839 A1    Dec. 23, 2010

(51) Int. Cl.
*G01N 29/12* (2006.01)
(52) U.S. Cl. ............... 702/56; 702/51; 702/54; 73/649; 73/40.5 R; 73/592; 340/605; 340/606
(58) Field of Classification Search ........... 702/51, 702/54, 56; 73/649, 152.58, 40, 40.5 A, 73/40.5 R, 592; 340/605, 683, 606
See application file for complete search history.

(56) References Cited

U.S. PATENT DOCUMENTS

| | | | |
|---|---|---|---|
| 4,166,393 A * | 9/1979 | Lindner et al. .................. | 73/579 |
| 4,289,030 A | 9/1981 | Alers et al. | |
| 4,845,989 A | 7/1989 | Titlow et al. | |
| 4,899,588 A | 2/1990 | Titlow et al. | |
| 5,362,962 A | 11/1994 | Barborak et al. | |
| 5,526,689 A | 6/1996 | Coulter et al. | |
| 5,987,990 A * | 11/1999 | Worthington et al. .......... | 73/592 |
| 6,995,677 B2 * | 2/2006 | Aronstam et al. ............. | 340/606 |
| 7,430,914 B2 * | 10/2008 | Mitchell et al. ................. | 73/649 |
| 7,668,670 B2 * | 2/2010 | Lander ............................ | 702/51 |
| 2002/0088281 A1 | 7/2002 | Gorman et al. | |

(Continued)

FOREIGN PATENT DOCUMENTS
EP    0593346 A    4/1994
(Continued)

OTHER PUBLICATIONS
U.S. Appl. No. 60/901,386.*
(Continued)

*Primary Examiner* — Carol Tsai
(74) *Attorney, Agent, or Firm* — The Ollila Law Group LLC

(57) ABSTRACT

A vibratory pipeline diagnostic system (100) is provided. The system (100) comprises at least one vibration generator (104) adapted to be affixed to a pipeline, at least one vibration sensor (107) adapted to be affixed to the pipeline, and a processing device (111) in communication with the at least one vibration generator (104) and the at least one vibration sensor (107). The processing device (111) is configured to vibrate a portion of the pipeline using the at least one vibration generator (104), receive a vibrational response to the vibration from the at least one vibration sensor (107), compare the vibrational response to one or more previous vibrational responses of the pipeline, and indicate a fault condition if the vibrational response differs from the one or more previous vibrational responses by more than a predetermined tolerance.

21 Claims, 2 Drawing Sheets

U.S. PATENT DOCUMENTS

| | | | |
|---|---|---|---|
| 2003/0101804 A1 | 6/2003 | Zanker | |
| 2004/0211272 A1 | 10/2004 | Aronstam et al. | |
| 2005/0060105 A1* | 3/2005 | Lander | 702/51 |
| 2005/0172697 A1 | 8/2005 | Nozaki et al. | |
| 2005/0279169 A1* | 12/2005 | Lander | 73/592 |
| 2006/0288756 A1* | 12/2006 | De Meurechy | 73/1.01 |
| 2007/0062291 A1* | 3/2007 | Mitchell et al. | 73/649 |
| 2010/0089161 A1* | 4/2010 | Taheri | 73/588 |

FOREIGN PATENT DOCUMENTS

| | | |
|---|---|---|
| FR | 2754898 A | 4/1998 |
| GB | 2083913 A | 3/1982 |
| GB | 2201777 A | 9/1988 |
| JP | 2004028907 A | 1/2004 |
| JP | 2006162391 | 6/2006 |
| WO | WO-92/09847 A | 6/1992 |
| WO | 03096007 A1 | 11/2003 |
| WO | WO 2005068886 A1 * | 7/2005 |

OTHER PUBLICATIONS

Cai Zhengmin et al. "Research on the Fault Diagnosis Mehtod for the Leakage Detection of Pipelines", Chinese Journal of Applied Mechanics, vol. 2, No. 2, pp. 38-43, Jun. 2002.

* cited by examiner

VIBRATORY PIPELINE DIAGNOSTIC SYSTEM AND METHOD

BACKGROUND OF THE INVENTION

1. Field of the Invention

The present invention relates to a pipeline diagnostic system and method, and more particularly, to a vibratory pipeline diagnostic system and method.

2. Statement of the Problem

Pipelines are used for transporting many types of gases and fluids. A pipeline, whether buried or above ground, can transport such materials for hundreds or even thousands of miles. Oil and natural gas pipelines are just two examples of materials that are transported via extensive networks of pipelines.

Pipelines are designed to be used for many years. However, they cannot last forever. If the material being transported is at least partially corrosive, then the wall of the pipeline can be gradually corroded away over time. This can lead to a weakening and ultimately to a rupture of the pipeline. In addition, if the material being transported includes solid particles, such as sand or other geological particles, the flowing material can erode the pipeline wall. This erosion process can also thin and weaken the pipeline wall.

Other damage to a pipeline is also possible. For example, machinery operating in the vicinity can impact and damage the pipeline. If a wall portion of the pipeline is deformed by an impact, the structural integrity of the pipeline will be affected. In addition, there is the possibility that inherent flaws in the pipeline wall can eventually manifest due to use of the pipeline, such as if the pipeline is pressurized to an appreciable pressure level.

There are many prior art diagnostic devices and methods that are available for checking on the condition of a pipeline. A pipeline can be visually inspected from the outside. However, this prior art method is very time-consuming, tedious, and expensive. In addition, such inspection may not be able to find flaws internal to the pipeline, such as corrosion and erosion, or at least until the problems become severe enough to cause a leak.

One prior art inspection device is referred to as a pig. A pig is an electronic inspection device that is passed through a section of pipeline. The pig can perform electronic scanning of the interior of the pipeline and can relay signals or data to an external station by wires or radio signals. However, a prior art pig has drawbacks, too. The prior art pig in some cases requires the material flow to be shut down and the pig transits the empty pipeline. Alternatively, the pig can be employed with the pipeline having material flow, wherein the pig is carried through the pipeline by the material flow. Some flow cessation may be required for the insertion and removal processes, however. As a consequence, the prior art pig requires cumbersome and time-consuming insertion and removal procedures.

Another prior art diagnostic device is shown in U.S. Patent Publ. 2005/0279169 to Lander. Lander includes an array of vibration sensors that are attached to the pipeline at intervals and discloses that a leak in a pipeline will cause a characteristic vibration to be produced. Lander discloses that the leak can be detected by detecting these characteristic vibrations. The drawback to this prior art approach is that the system is completely passive and cannot generate vibrations. In addition, the system of Lander cannot detect developing weaknesses in the pipeline, and cannot detect future flaws or problems in the pipeline. The system of Lander cannot detect or determine a problem until a leak develops. The system of Lander does not enable a pipeline to be maintained in order to prevent flaws or thinning in the pipeline from developing into serious leaks.

There remains a need for a diagnostic system and method for detecting structural degradation caused by corrosion, erosion, and other physical impacts in order to prevent leakage, avoid environmental impacts and impact costs, and minimize maintenance costs and downtime.

SUMMARY OF THE SOLUTION

A vibratory pipeline diagnostic system is provided according to an embodiment of the invention. The vibratory pipeline diagnostic system comprises at least one vibration generator adapted to be affixed to a pipeline, at least one vibration sensor adapted to be affixed to the pipeline, and a processing device in communication with the at least one vibration generator and the at least one vibration sensor. The processing device is configured to vibrate a portion of the pipeline using the at least one vibration generator, receive a vibrational response to the vibration from the at least one vibration sensor, and compare the vibrational response to one or more previous vibrational responses of the pipeline. The processing device is further configured to indicate a fault condition if the vibrational response differs from the one or more previous vibrational responses by more than a predetermined tolerance.

A vibratory diagnostic method for a pipeline is provided according to an embodiment of the invention. The method comprises vibrating a portion the pipeline, receiving a vibrational response to the vibration, comparing the vibrational response to one or more previous vibrational responses of the pipeline, and indicating a fault condition if the vibrational response differs from the one or more previous vibrational responses by more than a predetermined tolerance.

A vibratory diagnostic method for a pipeline is provided according to an embodiment of the invention. The method comprises vibrating a portion of the pipeline, receiving a vibrational response to the vibration, and determining a resonant frequency of the portion of the pipeline from the vibrational response. The method further comprises comparing the resonant frequency to one or more previous resonant frequencies of the pipeline and indicating a fault condition if the resonant frequency differs from the one or more previous resonant frequencies by more than a predetermined frequency tolerance.

ASPECTS

In one aspect of the system, the fault condition is related to a change in a wall thickness of the portion of the pipeline.

In another aspect of the system, the fault condition is related to a change in a wall structural integrity of the portion of the pipeline.

In yet another aspect of the system, the processing device is configured to store the vibrational response.

In yet another aspect of the system, the processing device is configured to transfer the vibrational response.

In yet another aspect of the system, the at least one vibration generator and the at least one vibration sensor are adapted to be removably affixed to the pipeline.

In yet another aspect of the system, the processing device is further configured to determine a resonant frequency of the portion of the pipeline from the vibrational response, compare the resonant frequency to one or more previous resonant frequencies of the pipeline, and indicate the fault condition if a difference between the resonant frequency and the one or more previous resonant frequencies exceeds a predetermined frequency tolerance.

In yet another aspect of the system, the system is configured to repeat the vibrating, receiving, and comparing at predetermined time intervals.

In one aspect of the method, the method further comprises repeating the vibrating, receiving, and comparing at predetermined time intervals.

In another aspect of the method, the fault condition is related to a change in a wall thickness of the portion of the pipeline.

In yet another aspect of the method, the fault condition is related to a change in a wall structural integrity of the portion of the pipeline.

In yet another aspect of the method, the method further comprises storing the vibrational response.

In yet another aspect of the method, the method further comprises transferring the vibrational response.

In yet another aspect of the method, the analyzing comprises determining a resonant frequency of the portion of the pipeline from the vibrational response, comparing the resonant frequency to one or more previous resonant frequencies of the pipeline, and indicating a fault condition if the resonant frequency differs from the one or more previous resonant frequencies by more than a predetermined frequency tolerance.

In yet another aspect of the method, the method further comprises storing the resonant frequency.

In yet another aspect of the method, the method further comprises transferring the resonant frequency.

DETAILED DESCRIPTION OF THE INVENTION

FIGS. 1-4 and the following description depict specific examples to teach those skilled in the art how to make and use the best mode of the invention. For the purpose of teaching inventive principles, some conventional aspects have been simplified or omitted. Those skilled in the art will appreciate variations from these examples that fall within the scope of the invention. Those skilled in the art will appreciate that the features described below can be combined in various ways to form multiple variations of the invention. As a result, the invention is not limited to the specific examples described below, but only by the claims and their equivalents.

Figure 1:
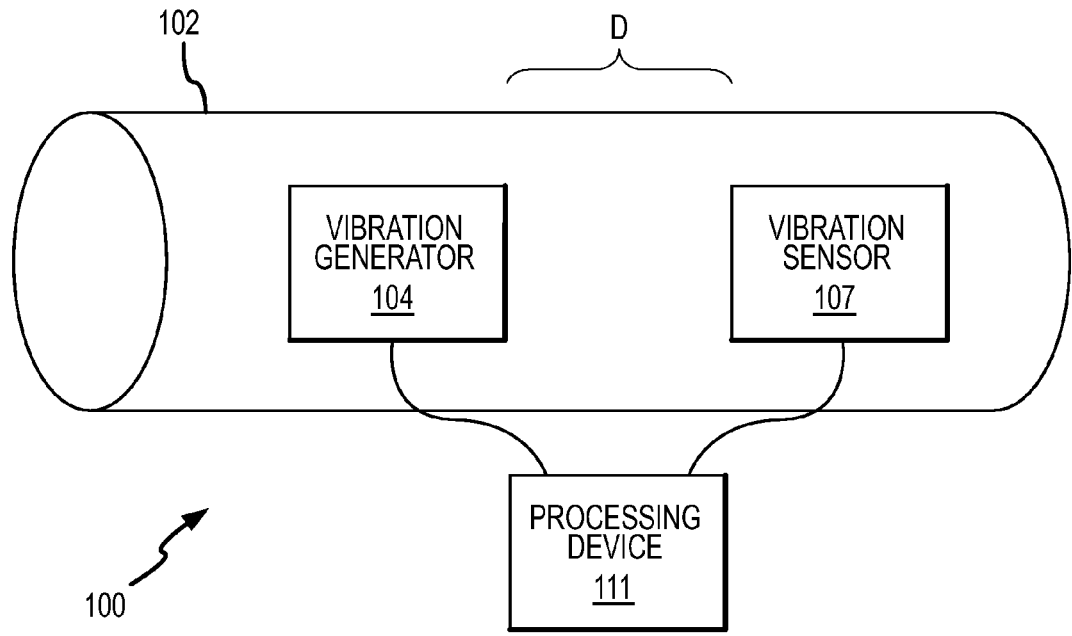
FIG. 1 shows a vibratory pipeline diagnostic system according to an embodiment of the invention.

FIG. 1 shows a vibratory pipeline diagnostic system 100 according to an embodiment of the invention. The vibratory pipeline diagnostic system 100 includes at least one vibration generator 104, at least one vibration sensor 107, and a processing device 111. The processing device 111 is in communication with the vibration generator 104 and the vibration sensor 107. The processing device 111 can be coupled to the vibration generator 104 and the vibration sensor 107 by any manner of wires, cables, etc., as shown in the figure. Alternatively, the processing device 111 can be coupled to the vibration generator 104 and the vibration sensor 107 by any manner of wireless link (not shown).

The vibration generator 104 and the vibration sensor 107 are affixed to a pipeline 102. The pipeline 102 can comprise a portion or section of pipe. The pipeline 102 can be of any diameter, length, or shape. The vibration generator 104 can be spaced apart from the vibration sensor 107, such as by a distance D. Alternatively, in another embodiment (not shown), the vibration generator 104 and the vibration sensor 107 can be closely located or can even comprise a unitary component affixed to a single location on the pipeline 102.

In some embodiments, the vibration generator 104 and the vibration sensor 107 are substantially permanently affixed to the pipeline 102. Alternatively, the vibration generator 104 and the vibration sensor 107 are removably affixed to the pipeline 102. The two components can be removably affixed in any manner, including through the use of fasteners, bands, clamps, adhesives, etc. In some embodiments, the processing device 111 is also removably or permanently affixed to the pipeline 102.

The processing device 111 is configured to vibrate a portion of the pipeline 102 using the vibration generator 104. The processing device 111 can send a drive signal to the vibration generator 104. The vibration generator 104 receives the drive signal from the processing device 111 and subsequently generates a vibration in the pipeline 102 according to the drive signal. The drive signal can include a predetermined frequency and amplitude, for example. The drive signal can include a predetermined plurality of frequencies, for example.

The processing device 111 is further configured to receive a vibrational response to the vibration. The vibrational response is generated by and received from the vibration sensor 107. The vibrational response comprises a measurement of the vibration of a portion of the pipeline 102 and is stimulated by the drive signal sent to the vibration generator 104.

The received vibrational response may be used to determine a fault condition in the pipeline 102. Consequently, the processing device 111 is further configured to compare the vibrational response to one or more previously obtained vibrational responses of the pipeline 102. The processing device 111 will indicate a fault condition if the vibrational response differs from the one or more previous vibrational responses by more than a predetermined tolerance. As a result, the processing device 111 can determine whether various fault conditions have occurred.

In one embodiment, the processing device 111 determines a resonant frequency of a portion of the pipeline 102 from the current vibrational response. If the wall thickness or structural integrity of the portion of the pipeline 102 has not changed, then the resonant frequency should not change. A change in the resonant frequency, however, can indicate there is a fault in the portion of the pipeline 102. For example, a change in the resonant frequency can be related to a change in a wall thickness of the portion of the pipeline 102. The pipeline wall thickness can decrease as a result of corrosion or erosion, including where a flow material in the pipeline 102 is corrosive or abrasive. In addition, a change in the resonant frequency can be related to a change in the wall structural integrity of the portion of the pipeline 102. For example, if the portion of the pipeline 102 has been hit or otherwise impacted, then the resonant frequency will change. An impact can dent or deform the pipeline 102. An impact can further cause cracks or other structural damage to the pipeline 102. If the pipeline has a crack or fissure, the resonant frequency will change.

The processing device 111 can include additional capabilities in some embodiments. The processing device 111 can store the current vibrational response and/or resonant frequency. The vibrational response/resonant frequency can be stored to serve as historical data in future computations and comparisons. This enables the processing device 111 to make comparisons at predetermined intervals and can track any corrosion or erosion occurring in the pipeline 102. The processing device 111 can also use the stored data to recognize the occurrence of structural damage to the pipeline 102. The stored data can also be used for future pipeline design, including for selection of a pipeline material and a wall thickness. In addition, it can be used to predict times for replacement or repair, for example.

The processing device 111 can further transmit data to other devices, including remote monitoring or data gathering devices. The data can include the vibrational response, the determined resonant frequency, and any determined fault condition, for example. The processing device 111 can transfer such information as it generated or upon request from another device.

The processing device 111 can be in communication with multiple vibration generators 104 and multiple vibration sensors 107. The processing device 111 can be designed to communicate with and control multiple such stations. Advantageously, the processing device 111 in this embodiment can reduce costs and components. In addition, the processing device 111 can be able to detect a spreading problem, such as corrosion or erosion that is moving downstream in the pipeline 102.

Figure 2:
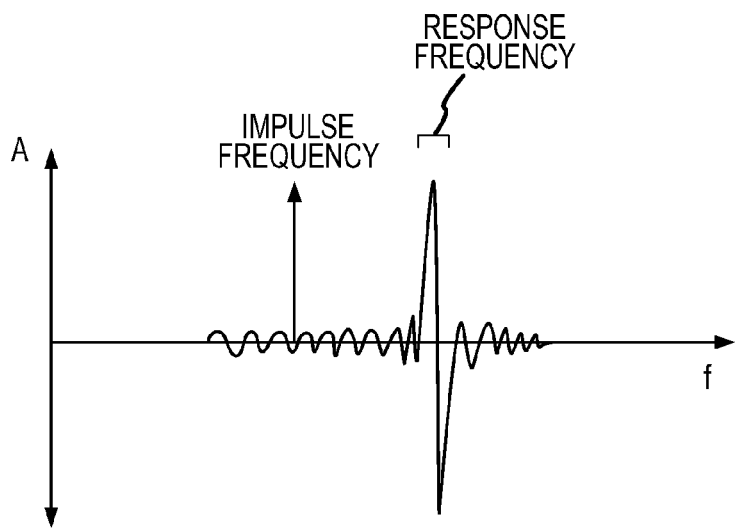
FIG. 2 is a graph of frequency (f) versus amplitude (A) in the pipeline that illustrates one method for determining the resonant frequency of the pipeline.

FIG. 2 is a graph of frequency (f) versus amplitude (A) in the pipeline that illustrates one method for determining the resonant frequency of the pipeline 102.

A vibration at a predetermined frequency is generated into the pipeline 102, as represented by the impulse frequency arrow. In response, the pipeline 102 will vibrate at a resonant frequency, such as the response frequency spike shown in the figure. It should be understood that the vibration generator 104 does not have to vibrate at the resonant frequency in order to produce the resonant frequency response in the pipeline 102.

The predetermined frequency can be at or near the resonant frequency. For example, the predetermined frequency can be generated at the resonant frequency of the pipeline when the pipeline was new, without the presence of any erosion, corrosion, or structural problems. Alternatively, the predetermined frequency can be generated at a previously determined resonant frequency (i.e., a previously stored value, for example).

Alternatively, the vibratory pipeline diagnostic system 100 can generate a frequency sweep. The frequency sweep can include a range of frequencies. The vibrational response can comprise vibrations of the pipeline 102, wherein the vibrational response will be much greater in amplitude at the resonant frequency.

Figure 3:
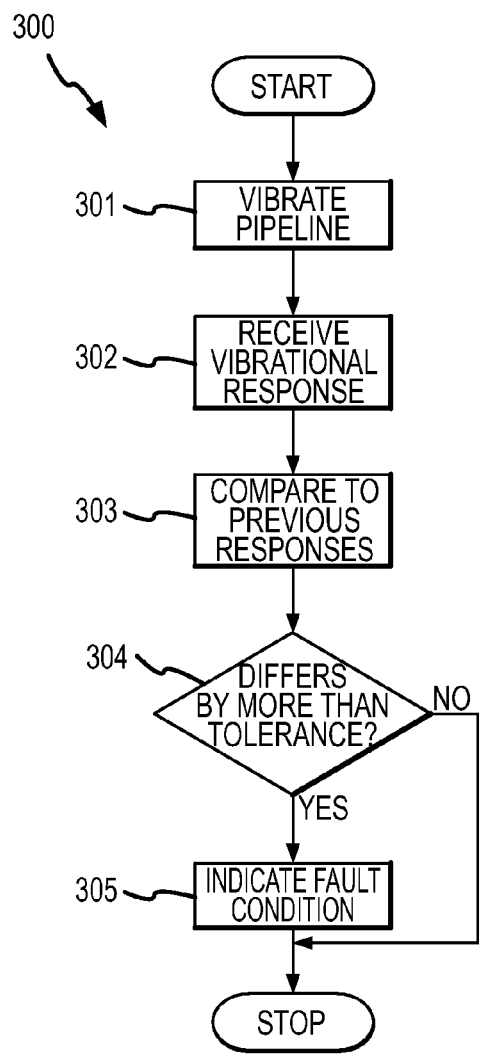
FIG. 3 is a flowchart of a vibratory diagnostic method for a pipeline according to an embodiment of the invention.

FIG. 3 is a flowchart 300 of a vibratory diagnostic method for a pipeline according to an embodiment of the invention. In step 301, a portion of the pipeline is vibrated. As previously discussed, the portion of the pipeline can be vibrated at about a resonant frequency, at an expected resonant frequency, or over a range of frequencies.

In step 302, a vibrational response is received from the portion of the pipeline. The vibrational response can include a plurality of frequencies and amplitudes.

In step 303, the vibrational response is compared to one or more previous vibrational responses. The one or more previous responses can be stored from previous diagnostic operations. As a result, the comparison can be used to determine if the pipeline has changed in condition over time.

In step 304, if the current vibrational response differs from the one or more previous responses by more than a predetermined tolerance, then the method proceeds to step 305. Otherwise, a fault is not indicated and the method branches around step 305.

In step 305, because the current vibrational response differs from the one or more previous responses by more than the predetermined tolerance, a fault condition is indicated. This can include setting a state, flag, or variable that reflects the fault condition. The fault condition can be stored and/or transferred to other devices. The fault condition can be further used to trigger an alarm, prompt inspection of the pipeline portion, etc.

The fault condition can further reflect a severity of the fault. For example, the fault condition can include levels that reflect the amount of change detected in the vibrational response.

The above steps can be repeatedly performed. The above steps can be performed at predetermined time intervals. For example, the steps can be performed at intervals that will ensure that any changes in wall thickness and/or wall structural integrity will be detected.

Figure 4:
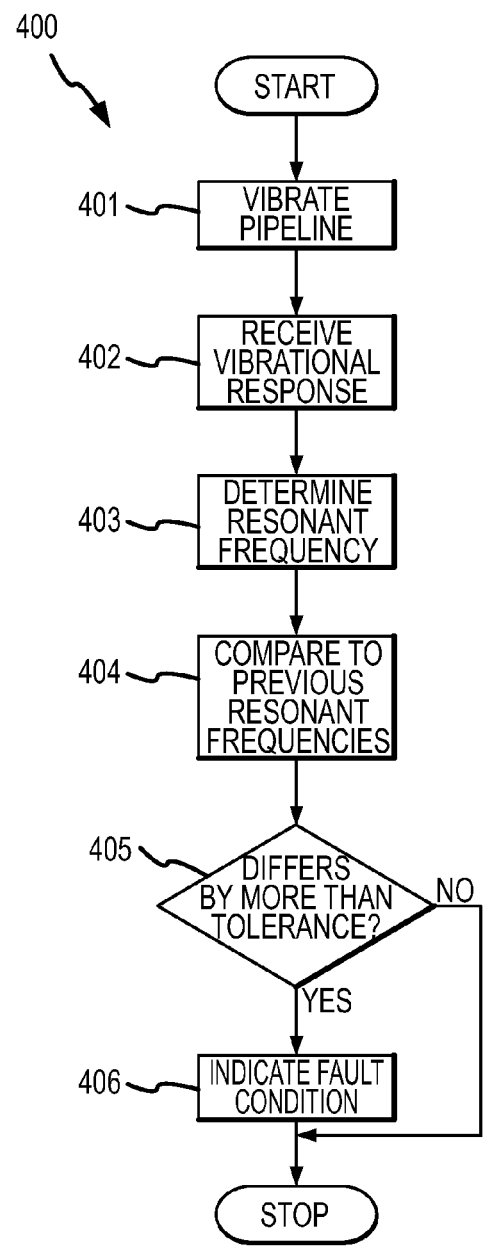
FIG. 4 is a flowchart of a vibratory diagnostic method for a pipeline according to an embodiment of the invention.

FIG. 4 is a flowchart 400 of a vibratory diagnostic method for a pipeline according to an embodiment of the invention. In step 401, a portion of the pipeline is vibrated, as previously discussed.

In step 402, a vibrational response is received from the portion of the pipeline. The vibrational response can include a plurality of frequencies and amplitudes. However, the vibrational response will likely include a resonant frequency that is detectably greater than surrounding frequencies.

In step 403, the resonant frequency of the portion of the pipeline is determined from the vibrational response. The resonant frequency in some embodiments is determined to be the maximum frequency response, as determined from the amplitude of the vibrational response (see FIG. 2). The resonant frequency comprises a natural vibration frequency of the pipeline, and can depend on factors such as the material of which the pipeline is constructed, the wall thickness, and the shape and size of the pipeline. Other factors may also influence the resonant frequency.

In step 404, the resonant frequency is compared to one or more previous resonant frequencies. The one or more previous resonant frequencies can be stored from previous diagnostic operations. As a result, the comparison can be used to determine if the pipeline has changed in condition over time.

In step 405, if the current resonant frequency differs from the one or more previous resonant frequencies by more than a predetermined frequency tolerance, then the method proceeds to step 406. Otherwise, a fault is not indicated and the method branches around step 406.

In step 406, because the current resonant frequency differs from the one or more previous resonant frequencies by more than the predetermined frequency tolerance, a fault condition is indicated. This can include setting a state, flag, or variable that reflects the fault condition. The fault condition can further reflect a severity of the fault. For example, the fault condition can include levels that reflect the amount of change detected in the resonant frequency. As previously discussed, the above steps can be repeatedly performed.

The vibratory pipeline diagnostic system and method can be employed according to any of the embodiments in order to provide several advantages, if desired. The vibratory pipeline diagnostic system and method provide a non-intrusive pipeline diagnostic capability that eliminates disruption to pipeline flow during a diagnostic process. The vibratory pipeline diagnostic system and method provide a diagnostic capability that can be performed without halting a material flow in the pipeline. The vibratory pipeline diagnostic system and method provide a diagnostic capability that can be performed without the need for inserting and removing diagnostic devices from the pipeline. The vibratory pipeline diagnostic system and method provide an ability to remotely monitor a pipeline. The vibratory pipeline diagnostic system and method can significantly reduce inspection costs and increase inspection frequency.

The vibratory pipeline diagnostic system and method provide a capability that can be used to monitor pipeline portions most likely to experience problems and leaks. The vibratory pipeline diagnostic system and method provide a diagnostic capability that can be performed at intervals. The vibratory pipeline diagnostic system and method provide a diagnostic capability that can be performed on demand and at any time. The vibratory pipeline diagnostic system and method provide an ability to monitor for changes on a more frequent and regular basis.

The vibratory pipeline diagnostic system and method provide a detection of structural integrity problems. The vibratory pipeline diagnostic system and method provide a detection of wall thinning.

The vibratory pipeline diagnostic system and method can prevent leakage. The vibratory pipeline diagnostic system and method can detect damage to a pipeline before leakage occurs. The vibratory pipeline diagnostic system and method can avoid environmental impacts and associated costs. The vibratory pipeline diagnostic system and method can minimize maintenance costs and downtime.

What is claimed is:

1. A vibratory pipeline diagnostic system (100), characterized by:
    at least one vibration generator (104) adapted to be affixed to a pipeline;
    at least one vibration sensor (107) adapted to be affixed to the pipeline; and
    a processing device (111) in communication with the at least one vibration generator (104) and the at least one vibration sensor (107), with the processing device (111) being configured to vibrate a portion of the pipeline using the at least one vibration generator (104), receive a vibrational response to the vibration from the at least one vibration sensor (107), compare the vibrational response to one or more previous vibrational responses of the pipeline, and indicate a fault condition if the vibrational response differs from the one or more previous vibrational responses by more than a predetermined tolerance.

2. The system (100) of claim 1, wherein the fault condition is related to a change in a wall thickness of the portion of the pipeline.

3. The system (100) of claim 1, wherein the fault condition is related to a change in a wall structural integrity of the portion of the pipeline.

4. The system (100) of claim 1, wherein the processing device (111) is configured to store the vibrational response.

5. The system (100) of claim 1, wherein the processing device (111) is configured to transfer the vibrational response.

6. The system (100) of claim 1, wherein the at least one vibration generator (104) and the at least one vibration sensor (107) are adapted to be removably affixed to the pipeline.

7. The system (100) of claim 1, with the processing device (111) being further configured to determine a resonant frequency of the portion of the pipeline from the vibrational response, compare the resonant frequency to one or more previous resonant frequencies of the pipeline, and indicate the fault condition if a difference between the resonant frequency and the one or more previous resonant frequencies exceeds a predetermined frequency tolerance.

8. The system (100) of claim 1, with the system (100) being configured to repeat the vibrating, receiving, and comparing at predetermined time intervals.

9. A vibratory diagnostic method for a pipeline, the method characterized by:
    vibrating a portion of the pipeline;
    receiving a vibrational response to the vibration;
    comparing the vibrational response to one or more previous vibrational responses of the pipeline; and
    indicating a fault condition if the vibrational response differs from the one or more previous vibrational responses by more than a predetermined tolerance.

10. The method of claim 9, further comprising repeating the vibrating, receiving, and comparing at predetermined time intervals.

11. The method of claim 9, wherein the fault condition is related to a change in a wall thickness of the portion of the pipeline.

12. The method of claim 9, wherein the fault condition related to a change in a wall structural integrity of the portion of the pipeline.

13. The method of claim 9, further comprising storing the vibrational response.

14. The method of claim 9, further comprising transferring the vibrational response.

15. The method of claim 9, with the analyzing comprising:
    determining a resonant frequency of the portion of the pipeline from the vibrational response;
    comparing the resonant frequency to one or more previous resonant frequencies of the pipeline; and
    indicating a fault condition if the resonant frequency differs from the one or more previous resonant frequencies by more than a predetermined frequency tolerance.

16. A vibratory diagnostic method for a pipeline, the method characterized by:
    vibrating a portion of the pipeline;
    receiving a vibrational response to the vibration;
    determining a resonant frequency of the portion of the pipeline from the vibrational response;
    comparing the resonant frequency to one or more previous resonant frequencies of the pipeline; and
    indicating a fault condition if the resonant frequency differs from the one or more previous resonant frequencies by more than a predetermined frequency tolerance.

17. The method of claim 16, further comprising repeating the vibrating, receiving, and comparing at predetermined time intervals.

18. The method of claim 16, wherein the fault condition is related to a change in a wall thickness of the portion of the pipeline.

19. The method of claim 16, wherein the fault condition is related to a change in a wall structural integrity of the portion of the pipeline.

20. The method of claim 16, further comprising storing the resonant frequency.

21. The method of claim 16, further comprising transferring the resonant frequency.

* * * * *